US012594072B2

(12) United States Patent
Tada et al.

(10) Patent No.: US 12,594,072 B2
(45) Date of Patent: Apr. 7, 2026

(54) MEDICAL SYSTEM

(71) Applicant: TERUMO KABUSHIKI KAISHA, Tokyo (JP)

(72) Inventors: Yuichi Tada, Santa Clara, CA (US); Yoichiro Kuwano, Machida Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 435 days.

(21) Appl. No.: 18/177,030

(22) Filed: Mar. 1, 2023

(65) Prior Publication Data

US 2023/0277173 A1     Sep. 7, 2023

(30) Foreign Application Priority Data

Mar. 4, 2022     (JP) ................................. 2022-033302

(51) Int. Cl.
*A61B 18/14*     (2006.01)
*A61B 17/068*     (2006.01)
*A61B 17/072*     (2006.01)

(52) U.S. Cl.
CPC ........ *A61B 17/068* (2013.01); *A61B 18/1445* (2013.01); *A61B 2017/07285* (2013.01)

(58) Field of Classification Search
CPC .......... A61B 17/3207; A61B 17/32075; A61B 17/320758; A61B 17/320725; A61B 17/320783
See application file for complete search history.

(56) References Cited

U.S. PATENT DOCUMENTS

| | | | |
|---|---|---|---|
| 2014/0012299 A1* | 1/2014 | Stoddard | ........ A61B 17/320092 606/169 |
| 2014/0316448 A1* | 10/2014 | Higgins | ......... A61B 17/320758 606/159 |
| 2019/0175211 A1* | 6/2019 | Carlson | ............ A61B 17/00234 |
| 2019/0201025 A1* | 7/2019 | Shelton, IV | ......... A61B 17/072 |
| 2019/0201051 A1* | 7/2019 | Narayanan | ............. A61B 90/06 |
| 2019/0262031 A1* | 8/2019 | Efremkin | ....... A61B 17/320758 |
| 2020/0054356 A1* | 2/2020 | Miller | ............ A61B 17/320758 |
| 2021/0007760 A1* | 1/2021 | Reisin | .................... G16H 40/63 |

FOREIGN PATENT DOCUMENTS

JP         2021-041197 A      3/2021

* cited by examiner

*Primary Examiner* — Diane D Yabut
(74) *Attorney, Agent, or Firm* — Kim & Stewart LLP

(57)     ABSTRACT

A medical system includes a device for removing an object in a body cavity, the device including a shaft portion including a rotatable drive shaft, a motor configured to rotate the drive shaft, and a cutter attached to a distal end of the drive shaft and configured to perform a cutting operation on the object when the drive shaft is rotated by the motor. The medical system further includes one or more sensors each configured to detect a physical quantity related to the cutting operation, and a controller configured to determine one or more cutting parameters for the cutting operation based on the physical quantity detected by each of the sensors, and control the motor to rotate the drive shaft according to the determined cutting parameters.

18 Claims, 5 Drawing Sheets

*FIG. 1*

MEDICAL SYSTEM

CROSS-REFERENCE TO RELATED APPLICATION(S)

This application is based on and claims the benefit of priority from Japanese patent application No. 2022-033302, filed Mar. 4, 2022, the entire contents of which are incorporated herein by reference.

BACKGROUND

Technical Field

Embodiments described herein relate generally to a medical system, a controller for a medical system, and a method carried out by a medical system.

Related Art

In recent years, medical devices for cutting a thrombus or the like from a biological body cavity such as a blood vessel have been used. One of such medical devices is an atherectomy device including a cutting unit for cutting a lesion such as plaque or a thrombus in the blood vessel.

SUMMARY

In a case where a lesion cannot be cut by an atherectomy device or the like in operation, the operator needs to adjust the cutting operation by increasing the rotational speed of the cutting unit or strongly pressing the cutting unit against the lesion. However, it is difficult for the operator to determine exactly how to adjust the operation according to various cutting situations, and it is difficult to appropriately operate the cutting unit.

Embodiments of the present invention provide a control device for a medical system, a medical system, and a control method performed by a medical system, in which appropriate cutting operation can be automatically performed according to a situation in a blood vessel.

In an embodiment, a medical system comprises a device for removing an object in a body cavity, the device including a shaft portion including a rotatable drive shaft, a motor configured to rotate the drive shaft, and a cutter attached to a distal end of the drive shaft and configured to perform a cutting operation on the object when the drive shaft is rotated by the motor. The medical system further includes one or more sensors each configured to detect a physical quantity related to the cutting operation, and a controller configured to determine one or more cutting parameters for the cutting operation based on the physical quantity detected by each of the sensors, and control the motor to rotate the drive shaft according to the determined cutting parameters.

In another embodiment, a controller for controlling a medical system including a device for removing an object in a body cavity is provided. The device includes a shaft portion including a rotatable drive shaft, a motor configured to rotate the drive shaft, and a cutter attached to a distal end of the drive shaft and configured to perform a cutting operation on the object when the drive shaft is rotated by the motor, and one or more sensors each configured to detect a physical quantity related to the cutting operation. The controller comprises a memory and a processor configured to determine one or more cutting parameters for the cutting operation based on the physical quantity detected by each of the sensors, store the determined cutting parameters in the memory, and control the motor to rotate the drive shaft according to the cutting parameters stored in the memory.

In yet another embodiment, a method carried out by a medical system is provided. The medical system includes a device for removing an object in a body cavity, the device including a shaft portion including a rotatable drive shaft, a motor configured to rotate the drive shaft, and a cutter attached to a distal end of the drive shaft and configured to perform a cutting operation on the object when the drive shaft is rotated by the motor, and one or more sensors each configured to detect a physical quantity related to the cutting operation. The method comprises determining one or more cutting parameters for the cutting operation based on the physical quantity detected by each of the sensors, and controlling the motor to rotate the drive shaft according to the determined cutting parameters.

According to the medical system, the controller, and the method as described above, the operation of the cutting unit can be controlled according to the detected physical quantity, and thus appropriate cutting operation can be automatically performed according to various situations in the blood vessel.

BRIEF DESCRIPTION OF DRAWINGS

FIG. 1 is an overall front view of a medical system according to a first embodiment.

DETAILED DESCRIPTION

Figure 2:
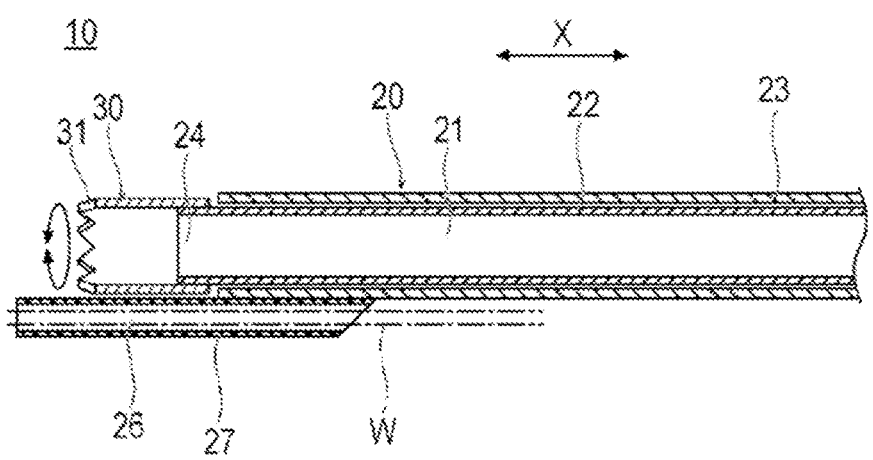
FIG. 2 is an enlarged cross-sectional view of a distal end portion of a medical device according to the first embodiment.

Hereinafter, embodiments of the present invention will be described with reference to the drawings. The size and ratio of each member in the drawings may be exaggerated for illustration purpose and may be different from the actual size and ratio.

First Embodiment

A medical system 1 according to the first embodiment includes a medical device 10 that is inserted into a blood vessel, and is used for a treatment to destroy and discharge a lesion such as thrombus, plaque, an atheroma, or a calcified lesion (hereinafter also referred to as an object) in an acute lower limb ischemia or a deep vein thrombosis. In the present specification, a side of the medical device 10 to be inserted into the blood vessel is referred to as a "distal side", and a side of the medical device 10 to be operated by the operator is referred to as a "proximal side". The object to be destroyed and discharged is not necessarily limited to the thrombus, the plaque, the atheroma, and the calcified lesion, and may be any object that can exist in the biological body cavity.

Figure 1:
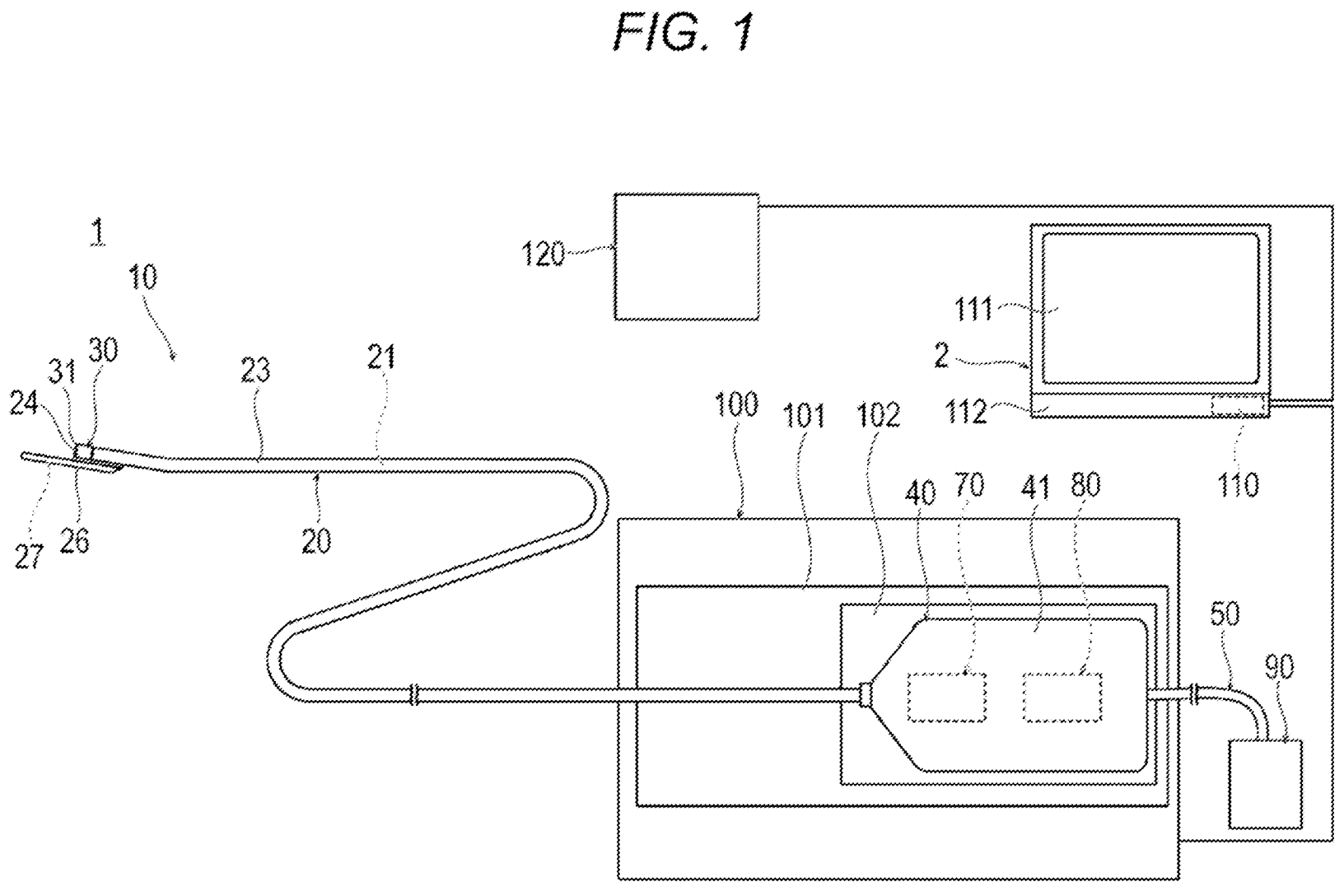
Figure 3:
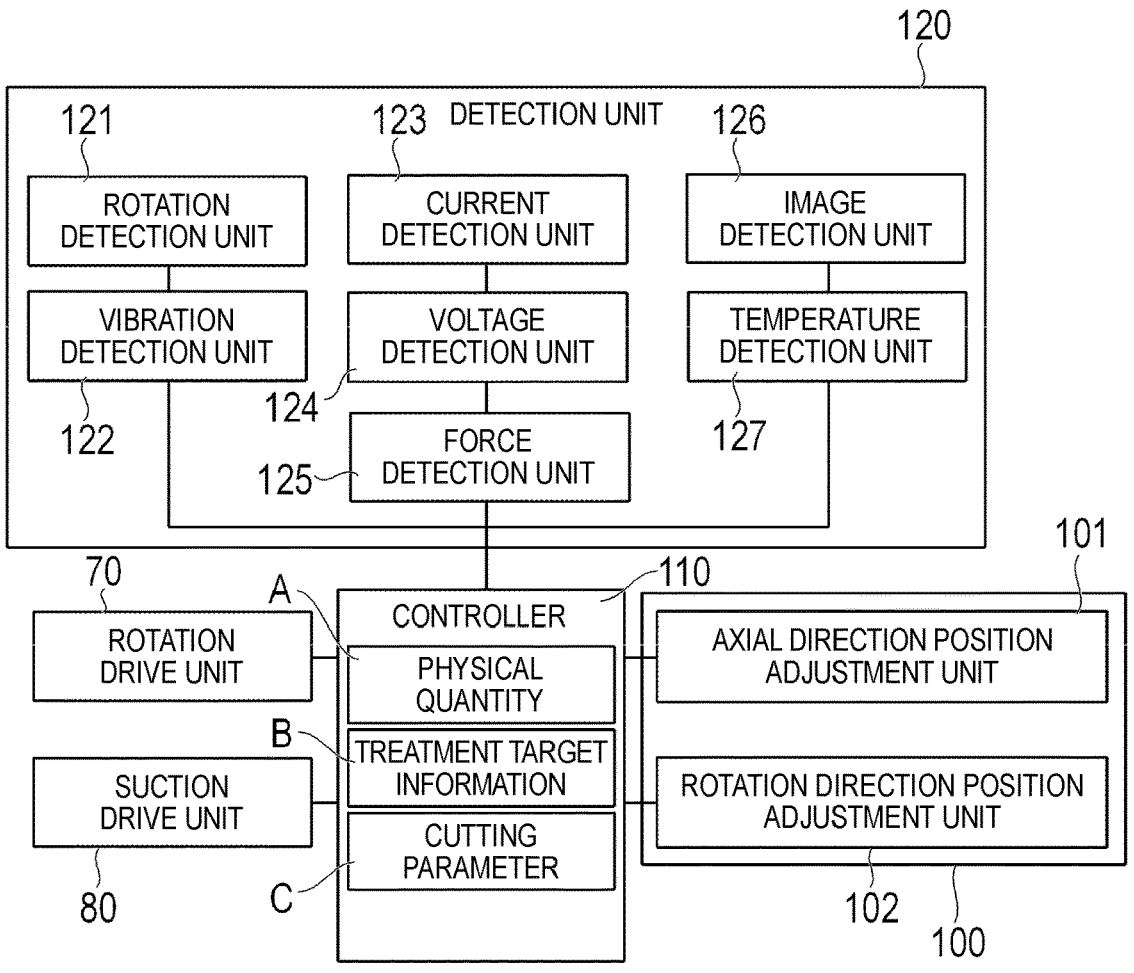
FIG. 3 is a hardware block diagram of the medical system according to the first embodiment.

As illustrated in FIGS. 1 to 3, the medical device 10 of the medical system 1 includes a cutting unit 30 disposed at a distal end portion for destroying the object, a position adjustment unit 100 that adjusts a position of the medical device 10 in the body cavity, a control device 2 including a controller 110 that controls operation of the medical device 10 and operation of the position adjustment unit 100, and a detection unit 120 that is positioned near the medical device 10 during a medical operation and detects various physical quantities (e.g., a rotation speed of the cutting unit 30) related to the operation of the medical system 1. The details of the physical quantities are described later.

The medical device 10 includes a long shaft portion 20 having a discharge lumen 21 through which an object can be carried to the proximal side, a cutting unit 30 disposed at a distal end portion of the shaft portion 20, and an operation unit 40 to which the proximal end portion of the shaft portion 20 is connected. The medical device 10 further includes a rotation drive unit 70 that rotates a drive shaft 22 provided in the shaft portion 20, a suction drive unit 80 that communicates with the discharge lumen 21 provided in the shaft portion 20, a discharge passage 50 through which a waste liquid sucked by the suction drive unit 80 is discharged, and a waste liquid bag 90 that communicates with the discharge passage 50 and receives the waste liquid through the discharge passage 50.

The shaft portion 20 includes the drive shaft 22 rotationally driven by the rotation drive unit 70, an outer tube 23 that rotatably accommodates the drive shaft 22, and a distal end tube 26 fixed to a side surface of a distal end portion of the outer tube 23.

The drive shaft 22 is connected to the cutting unit 30 and transmits a rotational force to the cutting unit 30. The drive shaft 22 is flexible and capable of transmitting rotational power acting from the proximal side to the distal side. The drive shaft 22 has the discharge lumen 21 formed for moving the cut object to the proximal side. The drive shaft 22 penetrates the outer tube 23, and has the cutting unit 30 fixed to the distal end portion of the drive shaft 22. The proximal end portion of the drive shaft 22 is connected to the rotation drive unit 70. The drive shaft 22 has a distal end opening 24 at the distal end at which the discharge lumen 21 is open. The distal end opening 24 is an inlet which debris, which is a suction target formed when being cut, enters. The proximal end portion of the drive shaft 22 is connected to the suction drive unit 80 that applies a suction force to the discharge lumen 21. The discharge lumen 21 may be formed not inside the drive shaft 22 but between the outer tube 23 and the drive shaft 22 or inside another tube provided inside the drive shaft 22.

The cutting unit 30 is a cutter that cuts an object such as a thrombus, plaque, or a calcified lesion to make the object small. Therefore, "cutting an object" means contacting an object and applying a force to the object so as to make the object small. The method of applying a force in cutting operation and the shape and form of the cut object are not limited. The cutting unit 30 has strength with which the above-described object can be cut. The cutting unit 30 is fixed to the distal end portion of the drive shaft 22. The cutting unit 30 includes a cylinder protruding toward the distal side of the drive shaft 22. The cutting unit 30 may be hollow and in communication with the discharge lumen 21. The distal end of the cutting unit 30 includes a sharp blade. The shape of the blade is not particularly limited. The cutting unit 30 may have a large number of fine abrasive grains instead of the blade.

The rotation drive unit 70 is disposed inside the operation unit 40 and rotates the drive shaft 22. The rotation drive unit 70 is, for example, a motor. The rotational speed of the rotation drive unit 70 is not particularly limited, and ranges from 5,000 rpm to 200,000 rpm, for example.

The suction drive unit 80 is disposed inside operation unit 40. The suction drive unit 80 is, for example, a pump, and communicates with the proximal end portion of the discharge lumen 21 of the drive shaft 22 to apply a suction force (i.e., negative pressure) to the discharge lumen 21. The suction drive unit 80 moves the waste liquid sucked through the discharge lumen 21 to the downstream side and discharges the waste liquid to the waste liquid bag 90. The suction drive unit 80 is, for example, a peristaltic pump, but may be a diaphragm pump. The peristaltic pump partially squeezes a tube containing the waste liquid with a plurality of rotating rollers, and moves a squeezing position to move the waste fluid inside the tube.

The outer tube 23 is a tube body having flexibility, and rotatably accommodates the drive shaft 22. The proximal end portion of the outer tube 23 is fixed to the operation unit 40. The outer tube 23 may have a bending portion that bends at a predetermined angle at a distal end portion thereof. Therefore, by rotating the outer tube 23, it is possible to change the orientation of the distal end portion of the outer tube 23 and easily bring the cutting unit 30 into contact with the object to be removed.

The distal end tube 26 is a tubular body having flexibility, and is fixed to the outer circumference surface of the distal end portion of the outer tube 23. The distal end tube 26 has a guide wire lumen 27 into which a guide wire can be inserted. When the outer tube 23 rotates, the position of the distal end tube 26 in the rotation direction of the outer tube 23 changes.

The discharge passage 50 is disposed between the suction drive unit 80 and the waste liquid bag 90, and conveys the waste liquid discharged from the suction drive unit 80 to the waste liquid bag 90. The discharge passage 50 is preferably transparent or translucent such that the operator can visually observe the internal flow.

The position adjustment unit 100 includes an axial direction position adjustment unit 101 that moves the shaft portion 20 in its axial direction X, and a rotation direction position adjustment unit 102 that rotates the shaft portion 20 about the axial direction X.

The axial direction position adjustment unit 101 is connected to the operation unit 40 and/or the shaft portion 20 of the medical device 10, and has a linear movement drive mechanism that linearly moves the operation unit 40 and/or the shaft portion 20 in the axial direction X. The linear movement drive mechanism may include a roller that rotates to move the shaft portion 20 in contact with the outer circumference surface thereof. The operation of the linear movement drive mechanism is controlled by the controller 110. Therefore, the axial direction position adjustment unit 101 can move the shaft portion 20 and the cutting unit 30 in the axial direction X according to instructions or control signals issued by the controller 110.

The rotation direction position adjustment unit 102 is connected to the operation unit 40 and/or the shaft portion 20 of the medical device 10, and has a rotation drive mechanism that rotates the operation unit 40 and/or the shaft portion 20 about the axial direction X. The operation of the rotation drive mechanism is controlled by the controller 110. Therefore, the rotation direction position adjustment unit 102 can rotate the shaft portion 20 about the axial direction X according to instructions or control signals issued by the controller 110. The position adjustment unit 100 including the axial direction position adjustment unit 101 and the rotation direction position adjustment unit 102 may be a three-dimensionally operable robot arm or the like.

The controller 110 includes a storage circuit and an arithmetic circuit. The storage circuit is, for example, a memory, and can store programs and various parameters. The arithmetic circuit is, for example, a processor such as a central processing unit (CPU), and can read programs and various parameters from the storage circuit to perform arithmetic processing.

The controller 110 further controls a display unit 111 such as a monitor that displays information as an image and an input unit 112 such as a touch panel, a keyboard, and/or a mouse such that the operator can perform operations and various settings.

The controller 110 controls operation of each of the rotation drive unit 70, the suction drive unit 80, the axial direction position adjustment unit 101, and the rotation direction position adjustment unit 102. The controller 110 calculates one or more cutting parameters C on the basis of one or more physical quantities A related to the cutting operation by the cutting unit 30, and treatment target information B acquired in advance, and controls the operation of the medical system 1 according to the calculated cutting parameters C.

The physical quantities A for cutting operation are classified into various types. For example, the physical quantities A related to the cutting operation are classified into the physical quantities A about the operation of the medical system 1 itself, the physical quantities A received by the medical system 1, and other physical quantities A.

The physical quantities A about the operation of the medical system 1 itself include the rotational speed of the cutting unit 30, sound and vibration generated by the cutting unit 30 and the rotation drive unit 70, a value of a current flowing to the rotation drive unit 70, the amount of energy supplied to the rotation drive unit 70, a temperature in the vicinity of the rotation drive unit 70, and the like.

The rotational speed of the cutting unit 30 is detected by a rotation detection unit 121 provided in the detection unit 120. The rotation detection unit 121 may be provided in the medical device 10 or the position adjustment unit 100. The rotation detection unit 121 may not directly detect the rotation of the cutting unit 30, but may detect the rotational speed of the drive shaft 22 or the rotation drive unit 70, and may specify the rotational speed of the cutting unit 30 from this result. The rotation detection unit 121 is not particularly limited, but for example, a tachometer of an optical type, a magnetic type, or the like can be applied.

The sound and vibration generated by the cutting unit 30 and the rotation drive unit 70 are detected by a vibration detection unit 122 provided in the detection unit 120 and positioned in the vicinity of the cutting unit 30 and the rotation drive unit 70 of the medical device 10 and the position adjustment unit 100. The vibration detection unit 122 is not particularly limited, and is, for example, a microphone that detects sound, an accelerometer that detects vibration, or the like.

The value of the current flowing to the rotation drive unit 70 is detected by a current detection unit 123 provided in detection unit 120. The current detection unit 123 may be provided in the medical device 10 or the position adjustment unit 100. The current detection unit 123 is, for example, an ammeter.

The amount of the energy supplied to the rotation drive unit 70 is detected by the current detection unit 123 and a voltage detection unit 124 which are provided in the detection unit 120. The current detection unit 123 and the voltage detection unit 124 may be provided in the medical device 10 or the position adjustment unit 100. The voltage detection unit 124 is, for example, a voltmeter.

The temperature in the vicinity of the rotation drive unit 70 is detected by a temperature detection unit 127 provided in the detection unit 120 and positioned in the vicinity of the medical device 10 and the rotation drive unit 70 of the position adjustment unit 100. The temperature detection unit 127 is, for example, a thermocouple sensor, an infrared temperature sensor, or the like.

The physical quantities A received by the medical system 1 include a reaction force received by the medical device 10, a frictional resistance value between the medical device 10 and the position adjustment unit 100, or the like.

The reaction force received by the medical device 10 is detected by a force detection unit 125 provided in the detection unit 120. The force detection unit 125 may be provided in the medical device 10 or the position adjustment unit 100. The force detection unit 125 is, for example, a gauge sensor or a piezoelectric sensor.

The frictional resistance value between the medical device 10 and the position adjustment unit 100 is detected by, for example, a gauge force sensor or a piezoelectric force sensor provided in the medical device 10 and the position adjustment unit 100.

The other physical quantities A include, for example, deformation of the shaft portion 20, the size or amount of the cut piece cut and sucked by the cutting unit 30, or the like.

The deformation of the shaft portion 20 is detected by, for example, an image detection unit 126 provided in the detection unit 120 and capable of imaging the shaft portion 20 in a body cavity. The image detection unit 126 may be provided in the medical device 10 or the position adjustment unit 100. The image detection unit 126 is, for example, a camera.

The image detection unit 126 may be used to detect the size or amount of the cut piece. In this case, the image detection unit 126 is disposed at a position at which the insides of the discharge passage 50 and the waste liquid bag 90 can be imaged from the outside.

The treatment target information B acquired in advance is, for example, the shape of a blood vessel or the shape of a lesion, the hardness of the lesion, or the like. The shape of the blood vessel or the shape of the lesion is detected by a known image recognition technology with a two-dimensional or three-dimensional image detected by, for example, intravascular ultrasound (IVUS), optical coherence tomography (OCT), imaging with a camera, ultrasonic diagnostic imaging, computed tomography (CT), magnetic resonance imaging (MRI), or the like.

The cutting parameters C include a movement distance of the shaft portion 20 in the axial direction X, a movement speed of the shaft portion 20 in the axial direction X, a rotational speed of the cutting unit 30 (or the rotation drive unit 70), a movement direction of the shaft portion 20 in the axial direction X, a cycle of a reciprocating movement of the shaft portion 20 in the axial direction X, and the like. At least one of the cutting parameters C may be one of the above-described physical quantities A related to the operation of the medical system 1.

The controller 110 calculates, determines, or selects the cutting parameters C based on the physical quantities A acquired during the operation of the medical device 10 and the treatment target information B acquired in advance. For example, the controller 110 can calculate and change the cutting parameters C in order to increase the cutting force by the cutting unit 30 or start cutting thereby or rotation thereof in a case where it is determined on the basis of the change in physical quantities A that the cutting unit 30 has come into contact with a lesion harder than the blood vessel or in a case where it is determined on the basis of the change in physical quantities A that the hardness or contact area of the lesion with which the cutting unit 30 comes into contact has increased. The controller 110 can calculate and change the cutting parameters C in order to reduce the cutting force in a case where it is determined on the basis of the change in physical quantities A that the cutting unit 30 in contact with the lesion no longer comes into contact with the lesion or in a case where it is determined on the basis of the change in physical quantities A that the hardness or amount of the lesion with which the cutting unit 30 comes into contact has decreased.

Examples of the change in physical quantities A with which it can be determined that the cutting unit 30 has come into contact with a lesion harder than the blood vessel or the hardness or contact area of the lesion with which the cutting unit 30 comes into contact has increased include, for example, a decrease in rotational speed detected by the rotation detection unit 121, an increase in amplitude or a decrease in frequency corresponding to the rotational speed which can be specified from sound or vibration detected by the vibration detection unit 122, an increase in current value detected by the current detection unit 123 (i.e., an increase in rotational resistance), an increase in energy amount specified from values detected by the current detection unit 123 and the voltage detection unit 124 (i.e., an increase in rotational resistance), an increase in temperature detected by the temperature detection unit 127 (i.e., an increase in rotational resistance), an increase in deformation amount of the shaft portion 20, which is detected by the image detection unit 126 (i.e., an increase in a reaction force), an increase in size and amount of the cut piece in the discharge passage 50 and the waste liquid bag 90, which is detected by the image detection unit 126, and an increase in a reaction force or frictional resistance value detected by the force detection unit 125.

The change of the cutting parameters C for improving the cutting force includes, for example, an increase in movement distance of the shaft portion 20 in the axial direction X, an increase in movement speed of the shaft portion 20 in the axial direction X, an increase in rotational speed of the cutting unit 30 (or the rotation drive unit 70), a change of the movement direction of the shaft portion 20 in the axial direction X, a decrease in cycle of the reciprocating movement of the shaft portion 20, and the like.

For example, the controller 110 can change the cutting parameters C in order to reduce the cutting force in a case where it is determined on the basis of the change in physical quantities A that the cutting unit 30 no longer comes into contact with the lesion or in a case where it is determined on the basis of the change in physical quantities A that the hardness or contact area of the lesion with which the cutting unit 30 comes into contact has decreased.

Examples of the change in physical quantities A with which it can be determined that the cutting unit 30 in contact with the hard lesion no longer comes into contact with a lesion or the hardness or contact area of the lesion with which the cutting unit 30 comes into contact has decreased include, for example, an increase in rotational speed detected by the rotation detection unit 121, a decrease in amplitude or an increase in frequency corresponding to the rotational speed which can be specified from sound or vibration detected by the vibration detection unit 122, a decrease in current value detected by the current detection unit 123 (i.e., a decrease in rotational resistance), a decrease in energy amount detected by the current detection unit 123 and the voltage detection unit 124 (i.e., a decrease in rotational resistance), a decrease in temperature detected by the temperature detection unit 127 (i.e., a decrease in rotational resistance), a decrease in deformation amount of the shaft portion 20, which is detected by the image detection unit 126 (i.e., a decrease in a reaction force), a decrease in size and amount of the cut piece in the discharge passage 50 and the waste liquid bag 90, which is detected by the image detection unit 126, and a decrease in a reaction force or frictional resistance value detected by the force detection unit 125.

In a case where it is determined that a stop condition for stopping cutting operation is satisfied on the basis of the change in physical quantities A, the controller 110 can stop the rotation drive unit 70 to stop the cutting operation. In the stop condition, for example, there is a case where the cutting of the lesion is completed and an object to be cut does not exist such that at least one change in the physical quantities A acquired before and after the cutting operation is completed becomes great and exceeds a preset threshold. The physical quantities A used for the stop condition may include, for example, the size or amount of the cut piece detected by the image detection unit 126. In this case, in a case where a new cut piece is not detected by the image detection unit 126, the controller 110 can determine that the cutting operation is completed and stop the cutting operation.

In a case where it is determined that a start condition for starting cutting operation is satisfied on the basis of the change in the physical quantities A, the controller 110 can control the rotation drive unit 70 to start the cutting operation. Examples of the start condition include an increase in a reaction force or frictional resistance value detected by the force detection unit 125.

In a case where it is determined that a blood vessel perforation due to the cutting unit 30 has occurred on the basis of the change in the physical quantities A, the controller 110 can control the rotation drive unit 70 to stop the rotation of the cutting unit 30 or reduce the rotational speed. An example of the change in the physical quantities A with which it can be determined that the blood vessel perforation due to the cutting unit 30 has occurred may include a case where at least one physical quantity A (for example, a reaction force) rapidly decreases after increasing, and then increases again. This is because it is considered that when the cutting unit 30 perforates the blood vessel, the resistance increases when the cutting unit 30 passes through the blood vessel wall, the resistance once sharply decreases after passing through the blood vessel wall, and the resistance increases again.

In a case where it is determined that the cutting unit 30 comes into contact with the lesion on the basis of the change in the physical quantities A, the controller 110 may control the axial direction position adjustment unit 101 to move the shaft portion 20 or the cutting unit 30 to the proximal side and then move the cutting unit 30 to the distal direction again. The controller 110 reciprocates the cutting unit 30 in the axial direction X, and applies an impact by causing the cutting unit 30 to come into contact with the lesion several times. Therefore, the cutting unit 30 can efficiently cut the lesion.

Figure 4:
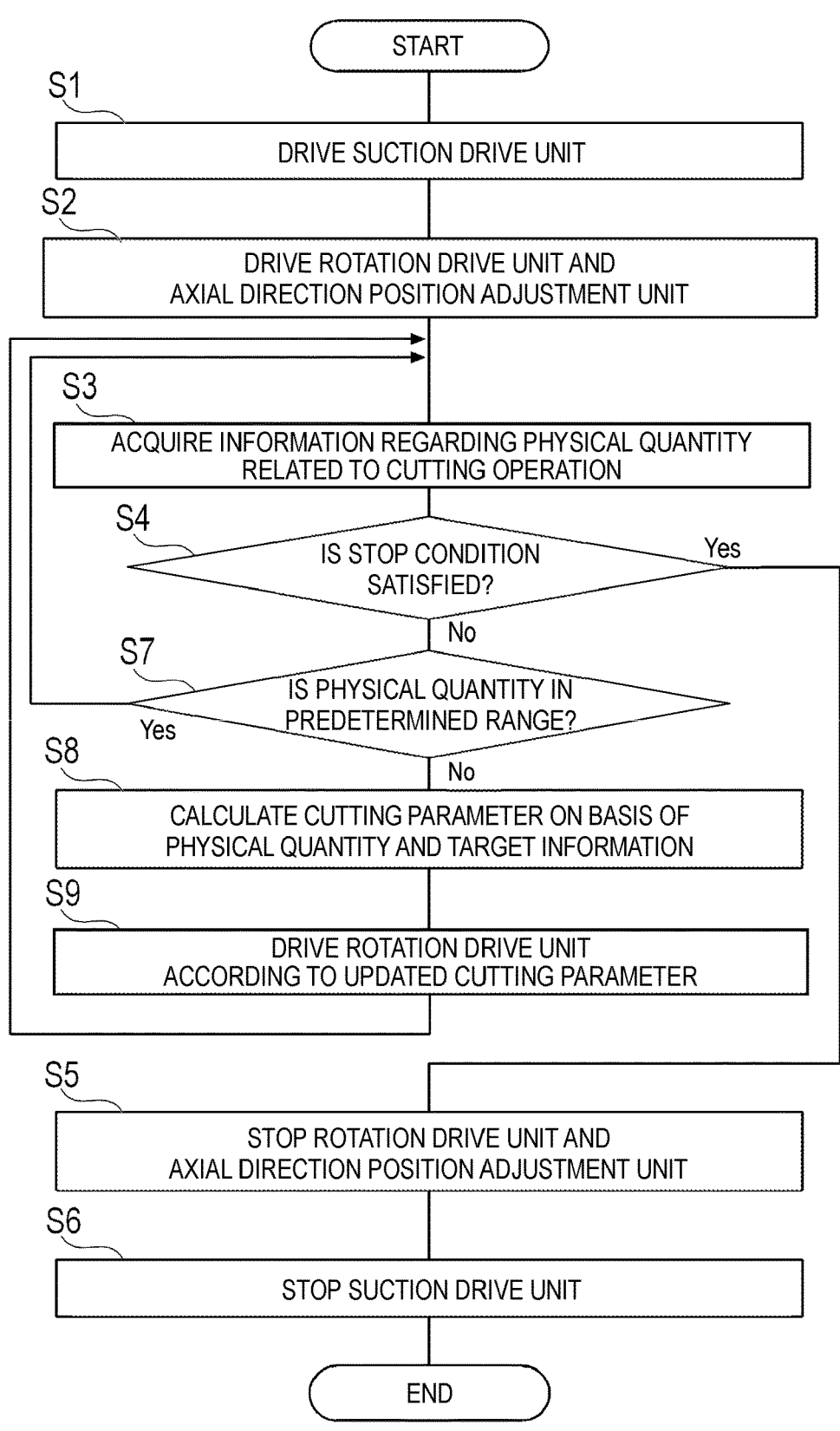
FIG. 4 is a flowchart illustrating operation of a controller according to the first embodiment.

Next, the operation control for the medical system 1 will be described with reference to the flowchart illustrated in FIG. 4.

Before performing a treatment for a patient using the medical system 1, the controller 110 stores treatment target information B of the patient. The treatment target information B acquired in advance includes, for example, a three-dimensional or two-dimensional image of a blood vessel and a lesion L to be removed, the hardness of the lesion L that can be specified from the image, or the like.

Figure 5:
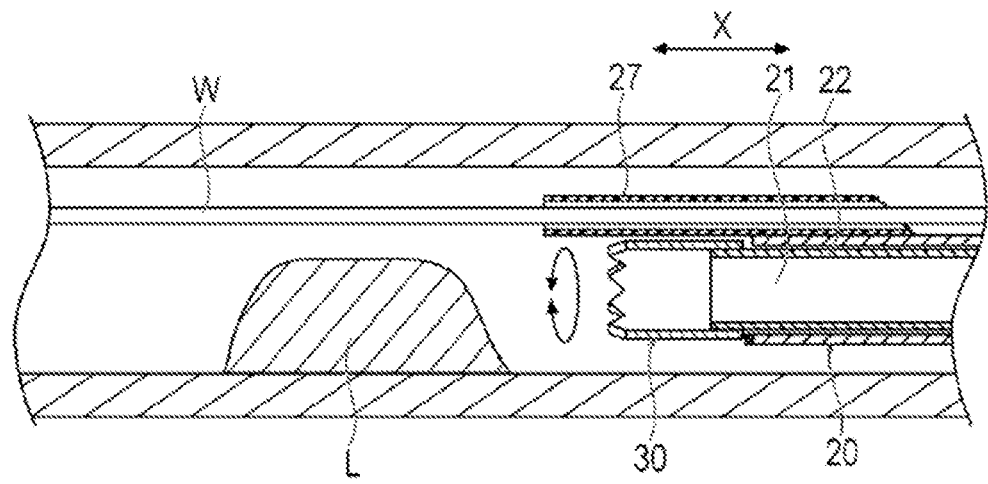
FIG. 5 is a cross-sectional view of the medical device with a cutting unit positioned near a lesion.

Next, the operator inserts the proximal end of a guide wire W into the guide wire lumen 27 of the medical device 10. Next, as illustrated in FIG. 5, the operator inserts the medical device 10 into the blood vessel by using the guide wire W as a guide. Thereafter, the operator moves the shaft portion 20 in the distal direction using the axial direction position adjustment unit 101 or manually until the cutting unit 30 reaches the vicinity of the lesion L.

Next, the operator operates the controller 110 to start control by the controller 110. The controller 110 drives the suction drive unit 80 under initially set cutting parameters C (S1). According to this, a suction force acts on the discharge lumen 21. Subsequently, while the cutting unit 30 is rotated at a predetermined rotational speed by the rotation drive unit 70 under the initially set cutting parameters C, the controller 110 causes the axial direction position adjustment unit 101 to adjust a movement distance of the cutting unit 30 in the axial direction X, a movement speed thereof in the axial direction X, a movement direction thereof along the axial direction X (i.e., the distal or proximal direction), and a cycle in a case where the cutting unit 30 is reciprocated in the axial direction X (S2).

Next, the controller 110 acquires information regarding the physical quantities A related to the cutting operation (S3). Specifically, the controller 110 receives signals indicating the physical quantities A from at least one of the tachometer, the vibration detection unit 122, the current detection unit 123, the voltage detection unit 124, the temperature detection unit 127, the force detection unit 125, or the image detection unit 126.

When determining that the change in the acquired physical quantities A satisfies the preset stop condition (S4), the controller 110 stops the rotation drive unit 70 to stop the rotation of the cutting unit 30, and causes the axial direction position adjustment unit 101 to stop the movement of the cutting unit 30 (S5).

Subsequently, the controller 110 stops the suction drive unit 80 to stop suction (S6). Therefore, the operation control for the medical system 1 by the controller 110 is completed. The controller 110 can also control the axial direction position adjustment unit 101 to stop the suction drive unit 80 and then automatically remove the medical device 10 from the blood vessel.

When determining that the change in the acquired physical quantities A does not satisfy the stop condition (S4), the controller 110 determines whether or not each of the acquired physical quantities A is within a predetermined range that is set in advance (S7).

When determining that each physical quantity A is within the predetermined range (S7), the controller 110 causes processing to return to processing of S3 while continuing the cutting operation without changing the cutting parameters C, and acquires information regarding the physical quantities A for the cutting operation again (S3).

When determining that one of the physical quantities A is not within the predetermined range (S7), the controller 110 calculates and updates the cutting parameters C on the basis of the physical quantity A for cutting operation and the treatment target information B acquired in advance (S8). Next, while the operation of the medical system 1 is controlled according to the updated new cutting parameters and the cutting unit 30 is rotated at a predetermined rotational speed by the rotation drive unit 70, the controller 110 causes the axial direction position adjustment unit 101 to control a movement distance of the cutting unit 30 in the axial direction X, a movement speed thereof in the axial direction X, a movement direction thereof in the axial direction X, and a cycle in a case where the cutting unit 30 is reciprocated in the axial direction X (S9). Subsequently, the controller 110 causes processing to return to S3, and acquires information regarding the physical quantities A for cutting operation again (S3). Thereafter, the controller 110 repeatedly executes steps of S3 to S4 and steps of S7 to S9 until the stop condition of S4 is satisfied.

As described above, according to the first embodiment, the control device 2 for the medical system 1 configured to cut an object in a blood vessel, includes the long shaft portion 20, the cutting unit 30 provided at a distal end portion of the shaft portion 20, at least one of the rotation drive unit 70 and the axial direction position adjustment unit 101, which is configured to operate the cutting unit 30, and the detection unit 120 configured to detect at least one physical quantity A of the medical system 1 for cutting operation, and the control device 2 includes the controller 110 configured to control the rotation drive unit 70 and/or the axial direction position adjustment unit 101, in which the controller 110 is capable of calculating at least one cutting parameter C on the basis of at least one physical quantity A, and controls the rotation drive unit 70 and/or the axial direction position adjustment unit 101 on the basis of at least one cutting parameter C.

According to the first embodiment, the medical system 1 configured to cut an object in a blood vessel includes the long shaft portion 20, the cutting unit 30 provided at a distal end portion of the shaft portion 20, at least one of the rotation drive unit 70 and the axial direction position adjustment unit 101, which is configured to operate the cutting unit 30, and the detection unit 120 configured to detect at least one physical quantity A of the medical system 1 for cutting operation, and the controller 110 configured to control the rotation drive unit 70 and/or the axial direction position adjustment unit 101, in which the controller 110 is capable of calculating at least one cutting parameter C on the basis of at least one physical quantity A, and controls the rotation drive unit 70 and/or the axial direction position adjustment unit 101 on the basis of at least one cutting parameter C.

In the control device 2 for the medical system 1 and the medical system 1 as described above, the operation of the cutting unit 30 can be controlled according to the detected physical quantity A, and thus appropriate cutting operation can be automatically performed on an object in a blood vessel according to a situation.

The controller 110 controls the rotation drive unit 70 that rotationally drives the cutting unit 30, and the cutting parameter C includes the rotational speed of the rotation drive unit 70. Therefore, the control device 2 for the medical system 1 can automatically perform appropriate cutting operation by controlling the rotation of the cutting unit 30 according to the detected physical quantity A, and thus the workability can be improved.

The controller 110 controls the axial direction position adjustment unit 101 that moves the cutting unit 30 in the axial direction of the shaft portion 20, and the cutting parameter C includes at least one of a movement distance of the cutting unit 30 moved by the axial direction position adjustment unit 101, a movement speed of the cutting unit 30 moved by the axial direction position adjustment unit 101, a movement direction of the cutting unit 30 moved by the axial direction position adjustment unit 101, or a cycle of the reciprocation in a case where the cutting unit 30 is reciprocated by the axial direction position adjustment unit 101. Therefore, the control device 2 for the medical system 1 can automatically perform appropriate cutting operation by controlling the movement of the cutting unit 30 in the axial direction X according to the detected physical quantity A, and thus the workability can be improved.

The physical quantity A includes at least one of the rotational speed of the cutting unit 30, the value of a current flowing to the rotation drive unit 70, the amount of energy supplied to the rotation drive unit 70, the temperature in the vicinity of the rotation drive unit 70, or the reaction force acting on the drive shaft 22 during the cutting operation. Therefore, the control device 2 for the medical system 1 can control the operation of the cutting unit 30 according to the physical quantity A sensitively changed according to a situation of the cutting operation, and automatically perform appropriate cutting operation.

The physical quantity A includes at least one of sound or vibration generated by the cutting unit 30 or the rotation drive unit 70. Therefore, the medical system 1 can control the operation of the cutting unit 30 according to the physical quantity A sensitively changed according to a situation of the cutting operation, and automatically perform appropriate cutting operation. Since the detection unit 120 can accurately detect sound or vibration generated by the cutting unit 30 or the rotation drive unit 70, the controller 110 can collect only the sound or vibration stored in advance by using, for example, a band pass filter or the like, or determine the sound or vibration having a specific frequency as noise. The specific frequency determined as noise is, for example, generated due to a conversation of a medical worker or the like, and is lower than the frequency generated by the rotation of the cutting unit 30.

The controller 110 determines whether or not at least one of the physical quantities A detected by the detection unit 120 is within a predetermined range, does not change the cutting parameter C in a case where the physical quantity A is within the predetermined range, and calculates and updates the cutting parameter C on the basis of the physical quantity A in a case where the physical quantity A exceeds the predetermined range. Therefore, the control device 2 for the medical system 1 does not change the cutting parameter C until it is necessary to change the cutting parameter C, and when it is necessary to change the cutting parameter C, the cutting parameter C is automatically and appropriately changed, and thus the lesion L can be always cut under an appropriate condition.

The controller 110 determines whether or not the change in at least one of the physical quantities A satisfies a preset stop condition, and stops the rotation drive unit 70 and/or the axial direction position adjustment unit 101 in a case where the stop condition is satisfied. Therefore, the control device 2 for the medical system 1 can cause the controller 110 to automatically determine to stop the operation.

Second Embodiment

Figure 6:
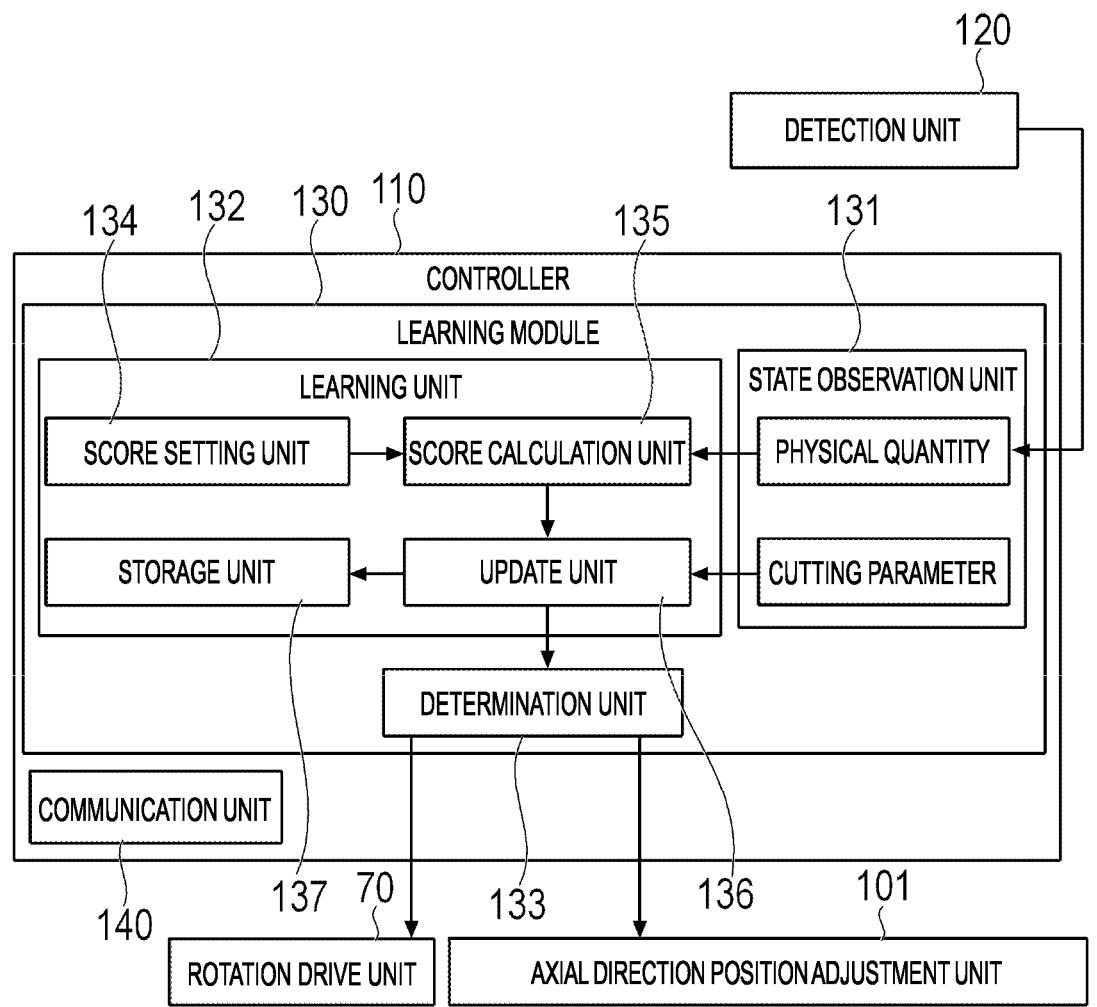
FIG. 6 is a functional block diagram of a controller of a medical system according to a second embodiment.

As illustrated in FIG. 6, a medical system 1 according to the second embodiment is different from that of the first embodiment in that the controller 110 includes a machine learning module 130 that performs machine learning and a communication unit 140 such as a network interface circuit connectable to a server for performing a machine learning operation.

Machine learning algorithms are generally classified into supervised learning, unsupervised learning, reinforcement learning, and the like. In the supervised learning algorithm, a set of input data and result data is given, and machine learning is performed on the basis of the set. In the unsupervised learning algorithm, only a large volume of data is given, and the machine learning is performed on the basis of the given data. The reinforcement learning algorithm changes an environment, which corresponds to the physical quantities A discussed above, on the basis of the solution, which corresponds to the cutting parameters C, output by the algorithm, and corrects the solution on the basis of a score as to how correct the output solution is. In the present embodiment, a case where reinforcement learning is performed as the machine learning will be described. Any machine learning other than the reinforcement learning may be used.

The machine learning module 130 includes a state observation unit 131, a learning unit 132, and a determination unit 133. The machine learning module 130 corresponds to an agent in reinforcement learning. The machine learning module 130 is included in the controller 110, but may be executed by, for example, an external device connectable to the medical system 1 according to the first embodiment.

The state observation unit 131 detects the state of the environment. The state observation unit 131 observes a state variable including at least one physical quantity A for cutting operation and at least one cutting parameter C. The state observation unit 131 stores the physical quantity A and the cutting parameter C in association with the observed time.

The learning unit 132 includes a score setting unit 134 that sets a score condition, a score calculation unit 135 that calculates a score, an update unit 136 that updates a function, and a storage unit 137 that stores a result obtained when the update unit 136 performs learning operation.

The score setting unit 134 sets a score condition. The score condition set by the score setting unit 134 is determined on the basis of, for example, the stability of the physical quantity A, the required cutting time taken until the cutting operation is completed after the start of the cutting operation, a cutting quality, energy consumption, and the like. For example, the score increases in a case where the physical quantity A is determined to be stable (i.e., variation in the physical quantity A is small), and the score decreases in a case where the physical quantity A is determined not to be stable. The score decreases in a case where the required cutting time is long, and the score increases in a case where the required cutting time is short. The score increases in a case where the cutting quality is improved, and the score decreases in a case where the cutting quality decreases. In order to perform such a determination, it is assumed that a device or software module capable of acquiring each data is provided, and an individual threshold or the like is set in advance for each data. The required cutting time can be specified by the controller 110, and the energy consumption can be specified by the current detection unit 123 and the voltage detection unit 124. The cutting quality can be calculated, for example, from an image obtained by the image detection unit 126. The score condition set by the score setting unit 134 may be determined on the basis of the stability of the physical quantity A for luminance of a cross-sectional image of the blood vessel, the required cutting time taken until the cutting operation is completed after the start of the cutting operation, a cutting quality, energy consumption, and the like. Therefore, the controller 110 can calculate the optimum cutting parameter C and state variable according to the physical quantity A for cutting operation with respect to the hardness of the blood vessel.

The score calculation unit 135 calculates a score on the basis of at least one physical quantity A and a score condition, which are observed by the state observation unit 131.

The update unit 136 updates a function for determining at least one cutting parameter C from the current state variable on the basis of the score calculated by the score calculation unit 135. The function is, for example, an action value function.

The determination unit 133 performs learning of selection of a high-value action. The determination unit 133 determines at least one cutting parameter C and an optimum correction amount of the cutting parameter C from the current state variable on the basis of the learning result of the learning unit 132.

The communication unit 140 can be connected to a server via a network. Thus, the controller 110 can perform at least part of high-load arithmetic processing in the machine learning using the server via the network. Therefore, the controller 110 of the medical system 1 or the control device 2 connectable to the server performs arithmetic processing for calculating the optimal action value function or the state variable by using the server via the network, receives an arithmetic result via the network, and optimally updates the arithmetic result.

Figure 7:
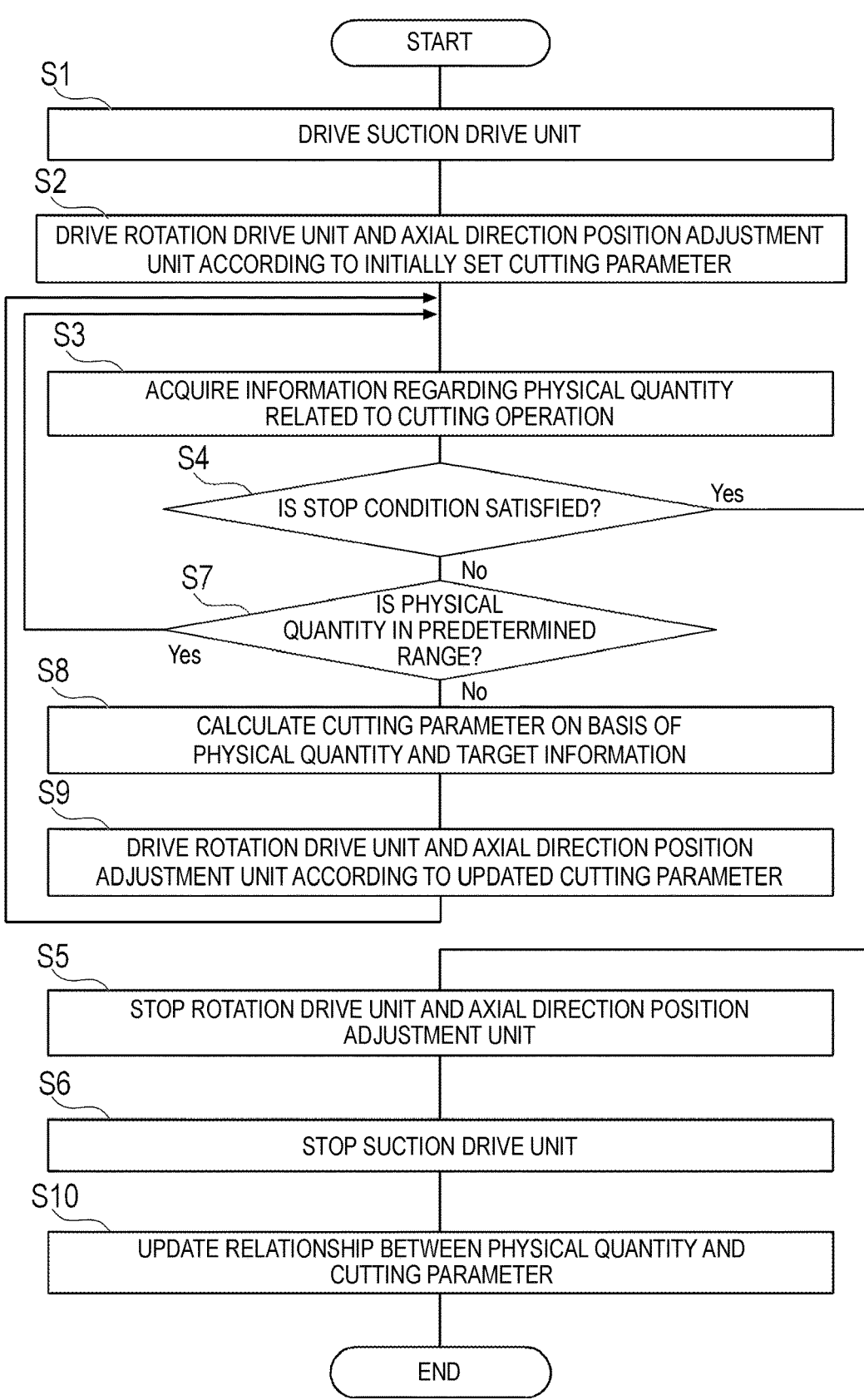
FIG. 7 is a flowchart illustrating operation of the controller according to the second embodiment.

As illustrated in FIG. 7, the processing of the machine learning module 130 is performed every time the lesion L is cut by the medical system 1 (S10). The machine learning module 130 calculates the score for each cutting parameter C by the score calculation unit 135, and updates the action value function with the update unit 136 such that the score increases. The update of the action value function can be performed by, for example, a known update formula used in Q-learning. Thus, the machine learning module 130 updates at least one cutting parameter C in order to cut the lesion L.

The reliability of the action value function is increased by repeatedly performing processing of the machine learning for each cutting operation. By using a highly reliable action value function, for example, at least one cutting parameter C can be made more optimal such that a Q-value used in the Q-learning increases. Therefore, when the cutting operation is performed, the optimum cutting parameter C can be automatically generated on the basis of the detected physical quantity A by using the action value function with increased reliability. The update of the action value function by the update unit 136 may be performed not for each procedure of cutting operation but during the procedure.

In the second embodiment, the controller 110 includes a learning unit 132 that performs learning of determining at least one cutting parameter C by updating a function for determining at least one cutting parameter C on the basis of a state variable having at least one physical quantity A and at least one cutting parameter C. The learning unit 132 includes a score calculation unit 135 that calculates a score for a result obtained by determining at least one cutting parameter C on the basis of the state variable, and an update unit 136 that updates the function on the basis of the score calculated by the score calculation unit 135, and performs learning of at least one cutting parameter C for which the score is most obtained when the update unit 136 repeats the update of the function. Therefore, the control device 2 for the medical system 1 can increase the reliability of the function for determining the cutting parameter C by repeatedly performing processing of the machine learning. At least one cutting parameter C can be made more optimal on the basis of a function with high reliability for determining the cutting parameter C.

The present invention is not limited to the above-described embodiments, and various modifications can be made by those skilled in the art within the technical idea of the present invention. For example, the cutting unit 30 may be, for example, a structure for performing cutting operation by moving the cutting unit in the axial direction X or a member for emitting a laser beam instead of a rotating body.

What is claimed is:

1. A medical system comprising:
   a device for removing an object in a body cavity, the device including:
      a shaft portion including a rotatable drive shaft,
      a motor configured to rotate the drive shaft, and
      a cutter attached to a distal end of the drive shaft and configured to perform a cutting operation on the object when the drive shaft is rotated by the motor;
   one or more sensors each configured to detect a physical quantity related to the cutting operation; and
   a controller configured to:
      determine one or more cutting parameters for the cutting operation based on the physical quantity detected by each of the one or more sensors, and
      control the motor to rotate the drive shaft according to the determined one or more cutting parameters, wherein
   one of the one or more sensors is configured to detect sound produced by the cutter or the motor,
   the controller is configured to determine the one or more cutting parameters based on the detected sound,
   the controller is configured to perform a machine learning algorithm to obtain a function suitable for determining the one or more cutting parameters from the physical quantity, the algorithm including:
      (a) determining first cutting parameters based on a first physical quantity using the function,
      (b) calculating a score for the first cutting parameters based on a second physical quantity that is detected after the cutting operation is performed according to the first cutting parameters, and
      (c) updating the function based on the calculated score, and
   the controller repeats steps (a)-(c) until the calculated score reaches a particular score.

2. The medical system according to claim 1, wherein the one or more cutting parameters include a rotational speed of the motor.

3. The medical system according to claim 1, further comprising:
   a roller configured to move the shaft portion along an axial direction thereof, wherein
   the controller is further configured to control the roller to move the shaft portion according to the determined one or more cutting parameters.

4. The medical system according to claim 3, wherein the one or more cutting parameters include at least one of:
   a movement distance of the shaft portion along the axial direction,
   a movement speed of the shaft portion along the axial direction,
   a direction toward which the shaft portion is moved along the axial direction, and
   a cycle of reciprocation motion of the shaft portion along the axial direction.

5. The medical system according to claim 1, wherein one of the one or more sensors is configured to detect at least one of:

a rotational speed of the cutter, a value of a current flowing in the motor, an amount of energy supplied to the motor, a temperature of the motor, and a reaction force acting on the shaft portion.

6. The medical system according to claim 1, wherein one of the one or more sensors is a microphone connectable to the controller.

7. The medical system according to claim 1, wherein the controller is further configured to:

determine whether a physical quantity detected by one of the one or more sensors has changed by a predetermined amount, and upon determining that the physical quantity has changed by the predetermined amount, update the one or more cutting parameters.

8. The medical system according to claim 1, wherein the controller is further configured to:

determine whether a stop condition is satisfied based on the physical quantity detected by each of the one or more sensors, and upon determining that the stop condition is satisfied, control the motor to stop.

9. The medical system according to claim 1, wherein the device further includes a pump configured to apply a suction force to a lumen of the shaft portion through which the cut object is moved, and the controller is further configured to control the pump to apply the suction force according to the determined one or more cutting parameters.

10. A medical system comprising:

a device for removing an object in a body cavity, the device including:

a shaft portion including a rotatable drive shaft, a motor configured to rotate the drive shaft, and a cutter attached to a distal end of the drive shaft and configured to perform a cutting operation on the object when the drive shaft is rotated by the motor;

one or more sensors each configured to detect a physical quantity related to the cutting operation; and a controller configured to:

determine one or more cutting parameters for the cutting operation based on the physical quantity detected by each of the one or more sensors, and control the motor to rotate the drive shaft according to the determined one or more cutting parameters, wherein the controller is further configured to execute a machine learning algorithm to generate a function suitable for determining the one or more cutting parameters from the physical quantity, and to iteratively update the function by:

(a) determining first cutting parameters based on a first physical quantity using the function, (b) calculating a score for the first cutting parameters based on a second physical quantity that is detected after the cutting operation is performed according to the first cutting parameters, and (c) updating the function based on the calculated score, and repeating steps (a)-(c) if the calculated score has not reached a particular score.

11. The medical system according to claim 10, wherein the one or more cutting parameters include a rotational speed of the motor.

12. The medical system according to claim 10, further comprising:

a roller configured to move the shaft portion along an axial direction thereof, wherein the controller is further configured to control the roller to move the shaft portion according to the determined one or more cutting parameters.

13. The medical system according to claim 12, wherein the one or more cutting parameters include at least one of:

a movement distance of the shaft portion along the axial direction, a movement speed of the shaft portion along the axial direction, a direction toward which the shaft portion is moved along the axial direction, and a cycle of reciprocation motion of the shaft portion along the axial direction.

14. The medical system according to claim 10, wherein one of the one or more sensors is configured to detect at least one of:

a rotational speed of the cutter, a value of a current flowing in the motor, an amount of energy supplied to the motor, a temperature of the motor, and a reaction force acting on the shaft portion.

15. The medical system according to claim 10, wherein one of the one or more sensors is configured to detect at least one of:

sound produced by the cutter or the motor, and vibration produced by the cutter or the motor.

16. The medical system according to claim 10, wherein the controller is further configured to:

determine whether a physical quantity detected by one of the one or more sensors has changed by a predetermined amount, and upon determining that the physical quantity has changed by the predetermined amount, update the one or more cutting parameters.

17. The medical system according to claim 10, wherein the controller is further configured to:

determine whether a stop condition is satisfied based on the physical quantity detected by each of the one or more sensors, and upon determining that the stop condition is satisfied, control the motor to stop.

18. The medical system according to claim 10, wherein the device further includes a pump configured to apply a suction force to a lumen of the shaft portion through which the cut object is moved, and the controller is further configured to control the pump to apply the suction force according to the determined one or more cutting parameters.

* * * * *